(12) United States Patent
Robinson

(10) Patent No.: US 6,890,740 B2
(45) Date of Patent: May 10, 2005

(54) METHOD AND APPARATUS FOR BIOLOGICAL MATERIAL SEPARATION

(75) Inventor: Donna L. Robinson, Los Alamos, NM (US)

(73) Assignee: The Regents of the University of California, Los Alamos, NM (US)

( * ) Notice: Subject to any disclaimer, the term of this patent is extended or adjusted under 35 U.S.C. 154(b) by 743 days.

(21) Appl. No.: 09/782,324

(22) Filed: Feb. 12, 2001

(65) Prior Publication Data

US 2002/0110923 A1 Aug. 15, 2002

(51) Int. Cl.$^7$ .................................................. C12N 5/00
(52) U.S. Cl. ................ 435/91.1; 435/304.1; 435/317.1; 210/781; 422/72; 436/177
(58) Field of Search ............................ 435/91.1, 317.1, 435/304.1, 177; 422/72; 210/781

(56) References Cited

U.S. PATENT DOCUMENTS

| | | | | |
|---|---|---|---|---|
| 5,225,332 A | * | 7/1993 | Weaver et al. ................ | 435/29 |
| 5,508,164 A | * | 4/1996 | Kausch et al. ................ | 435/6 |
| 5,654,179 A | * | 8/1997 | Lin ............................ | 435/91.2 |
| 5,665,582 A | * | 9/1997 | Kausch et al. .............. | 435/181 |
| 6,120,985 A | * | 9/2000 | Laugharn et al. ............ | 435/1.3 |
| 6,121,054 A | * | 9/2000 | Lebl ............................ | 436/177 |
| 6,129,828 A | * | 10/2000 | Sheldon et al. ............. | 204/518 |

* cited by examiner

Primary Examiner—Leon B. Lankford, Jr.
(74) Attorney, Agent, or Firm—Genma Morrison Bennett; Mark N. Fitzgerald

(57) ABSTRACT

There has been invented an apparatus comprising a separation barrier for excluding denser cell materials from less dense cell materials after centrifuging of the cells so that selected materials can be withdrawn from the less dense cell materials without inclusion of the denser cell materials or clogging of sampling equipment with denser cell materials. Cells from which selected material is to be withdrawn are centrifuged, either as cells or cells in media. Once the denser cell materials are isolated in a layer by centrifugal force, an invention screen or seive is submerged in the less dense cell material to a level above the layer of denser cell materials to isolate the denser cell materials from the less dense cell materials, preventing mixing of the denser cell materials back into the less dense cell materials when the cells or the cells in media are no longer being centrifuged and to prevent clogging of sampling equipment with denser cell materials. In a particularly useful application of the invention method and apparatus, plasmid DNA can be withdrawn from less dense cell materials without contamination or interference with denser cell materials.

5 Claims, 3 Drawing Sheets

METHOD AND APPARATUS FOR BIOLOGICAL MATERIAL SEPARATION

This invention was made with government support under Contract No. W-7405-ENG-36 awarded by the U.S. Department of Energy. The government has certain rights in the invention.

TECHNICAL FIELD

This invention relates to an apparatus and method for maintaining separation of less dense biological materials from more dense biological materials after centrifuging is completed.

BACKGROUND ART

There have been developed various apparatuses and methods for separating components of biological materials. Many of the methods rely on centrifuging the biological materials and any fluids used to treat the cells or as solvents or carriers. When uncontaminated samples of supernatant are to be taken from centrifuged biological materials including cells, the samples must be taken before chains in the denser cell materials begin to relax and the denser cell materials begin to migrate up into the supernatant layer of the centrifuged solution, thereby building time constraints into production processes. Commonly used methods include simply aspirating the supernatant obtained by centrifuging a mixture or solution of the biological material and withdrawing samples of supernatant before migration of the denser materials into the supernatant layer. In other methods, liquids or supernatant containing the biological material are passed through any of a large variety of strainers or filters.

Other more complicated methods have been used to separate biological materials.

For example, U.S. Pat. No. 6,129,828 issued Oct. 10, 2000 to Sheldon et al., discloses electrophoresis of biological samples to utilize the differential charge-to-mass ratio of sample constituents so as to control the migration of materials within a solution.

Another method for isolation and sorting of biological materials involves anchoring of biological material which has been separated from cellular milieu to a support such as glass coverslips, glass or polymer beads, then labeling the biological material in the polymerized or cross-linked system with magnetic particles. The magnetic particle properties are then exploited for isolation of the biological material. An example of this method is disclosed in U.S. Pat. No. 5,665,582, issued to Kausch and Narayanswami Sep. 9, 1997.

There is still a need for a simple, easy way to cleanly separate biological materials.

Therefore, it is an object of this invention to provide a method and apparatus for separation of biological materials.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

DISCLOSURE OF INVENTION

To achieve the foregoing and other objects, and in accordance with the purposes of the present invention, as embodied and broadly described herein, there has been invented a separation barrier having a screen, mesh or sieve for excluding denser biological materials from less dense biological materials after centrifuging of the biological materials. The separation barrier enables withdrawal of selected materials from the supernatant without inclusion of the denser biological materials or clogging of sampling equipment with denser biological materials.

Biological materials from which selected material is to be withdrawn are centrifuged, either with or without media such as lysing solutions, markers, binding compositions, solvents or solutions of other agents used to treat or process the biological materials. Once the denser biological materials are concentrated or aggregated by centrifugal force, into a discrete layer, an invention separation barrier is submerged in the less dense biological material to a level above the layer of denser biological materials to isolate the denser biological materials from the supernatant containing the less dense biological materials. The separation barrier prevents migration of the denser biological materials back into the supernatant containing the less dense biological materials when the biological materials are no longer being centrifuged. The separation of the supernatant from the denser biological materials prevents clogging of sampling equipment with denser biological materials and enables collection of uncontaminated clean catch samples.

In one particularly useful application of the invention method and apparatus, supernatant containing plasmid DNA can be withdrawn from a centrifuged sample without interference or contamination with denser cell materials.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

BEST MODES FOR CARRYING OUT THE INVENTION

It has been discovered that rather than filtering, straining, binding, or otherwise processing denser biological materials to separate them from less dense biological materials, a separation barrier having a screen, mesh or sieve projecting in a conformation that will fit into a container in which biological material is centrifuged can be used to isolate the layer of denser materials which results from centrifuging the biological material from the supernatant. For convenience the terms "screen," "mesh" or "sieve" will be referred to herein as "mesh". A single mesh such as a stiff net or, alternatively, an array of meshes designed to fit into an array of centrifuge containers such as the wells in a microtiter plate, can be used to separate biological materials in accordance with the invention.

When the biological material from which one or more components are to be separated is centrifuged, a layer of denser materials such as broken cell walls, cell membranes, mitochondria and ribosomes forms at the outermost position of the centrifuge container, leaving an upper portion (supernatant) of less dense material having water, enzymes, soluble proteins and small DNA fragments. If the biological material such as cells are centrifuged in media, then the upper portion or layer of the centrifuged product may also contain liquid media, such as enzymes used to treat the cells in the media such as when the cells are lysed for plasmid DNA collection or treated with other agents for other purposes.

Figure 1:
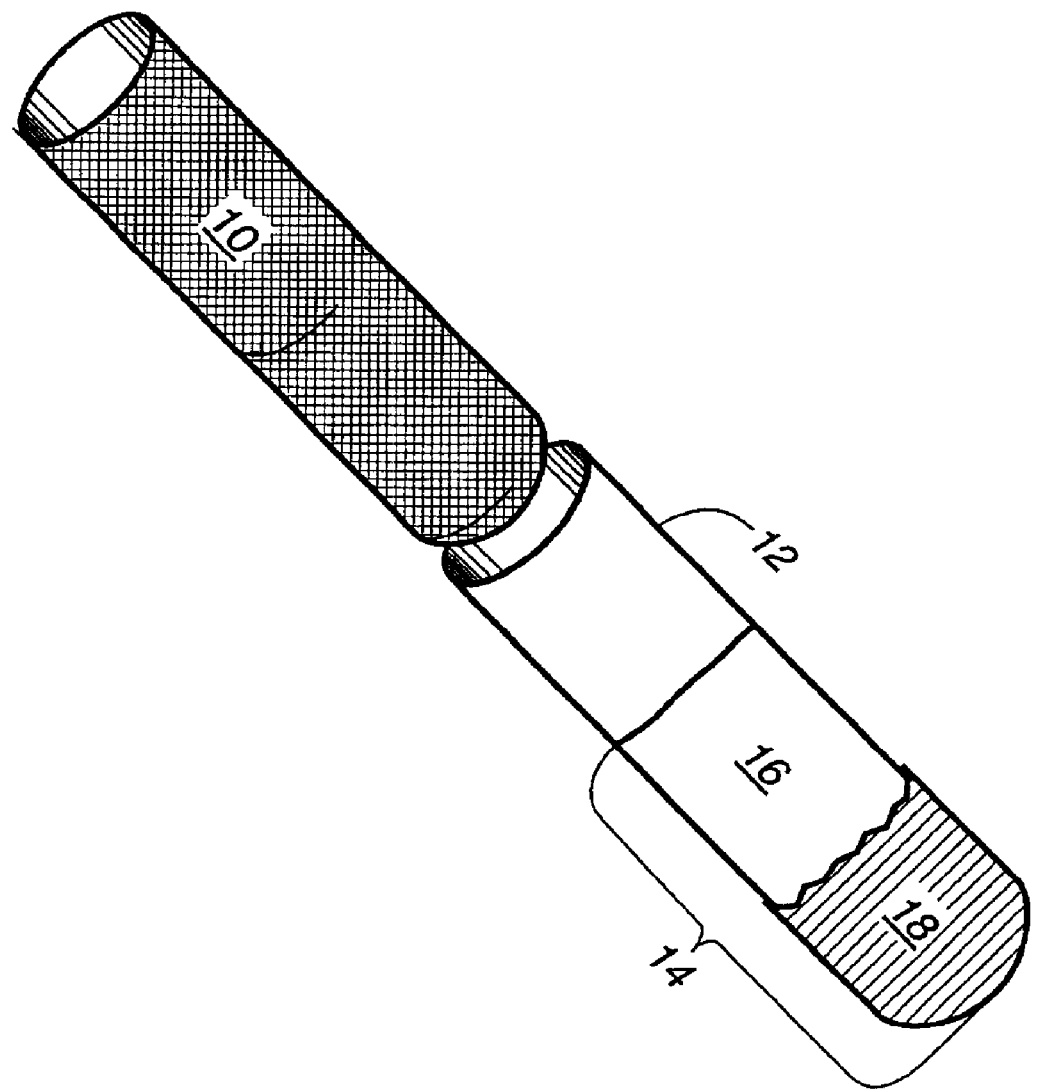
FIG. 1 is an isometric schematic of an invention separation barrier and centrifuge sample container.

In a simple embodiment of the invention, a meshed well or a well having a bottom that has an open mesh can be used without a barrier plate as shown in FIG. 1. These can be essentially simple stiff net structures with a meshed well shaped to fit within a container 12 having a centrifuged sample 14 of denser materials 16 with a supernatant 18 therein. Single meshed wells or wells with bottom portions which are meshed are preferred when samples in a single individual vessel such as a centrifuge tube are being separated. The meshed well 10 can be gripped on the portion of it extending above the top of the sample container 12 when the lower portion of the meshed well 10 is submerged in the supernatant 16.

Figure 2:
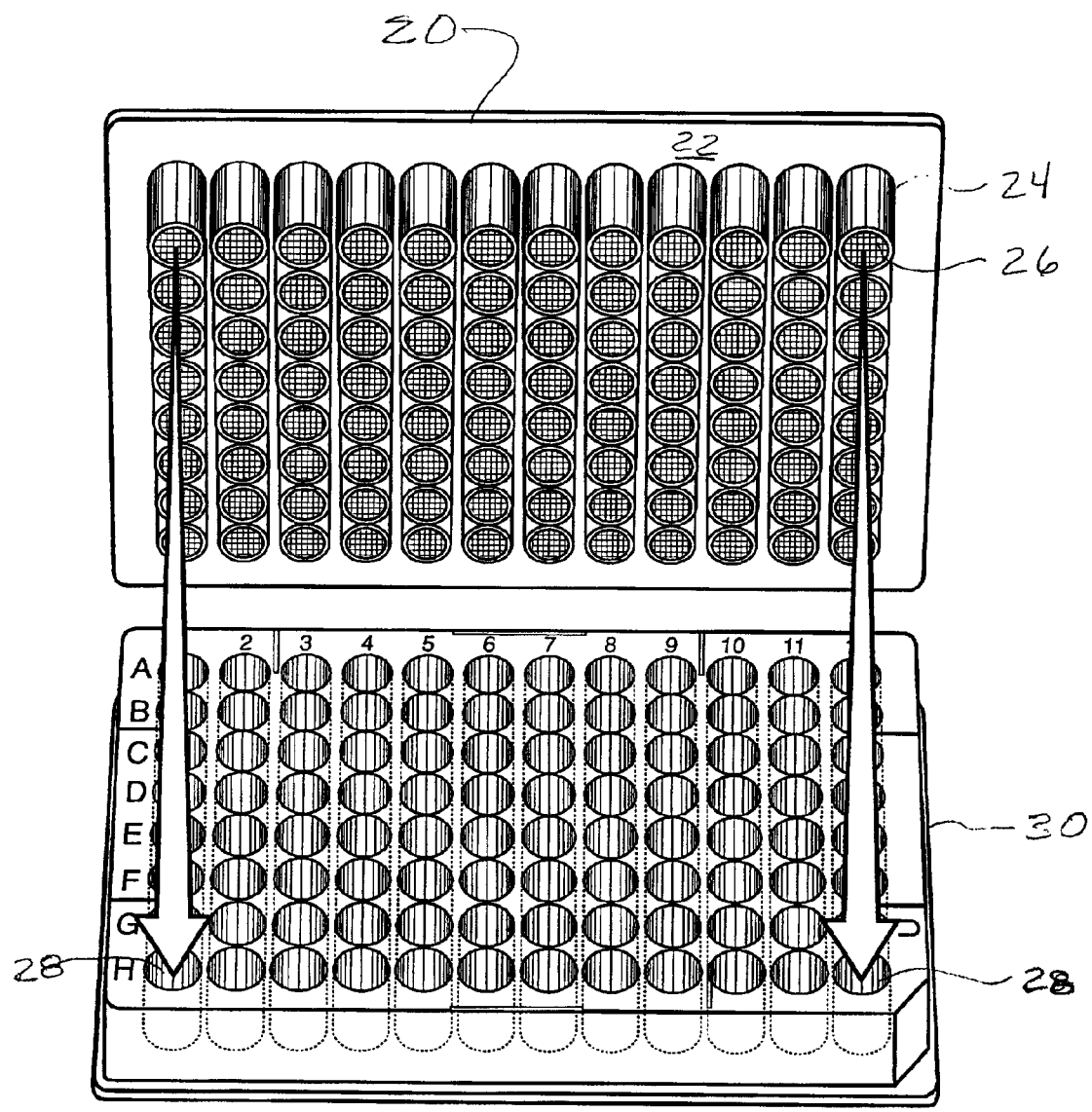
FIG. 2 is an isometric schematic of an invention separation barrier having a barrier plate and an array of barrier meshes adapted for use with a microtiter plate, also shown.
Figure 3:
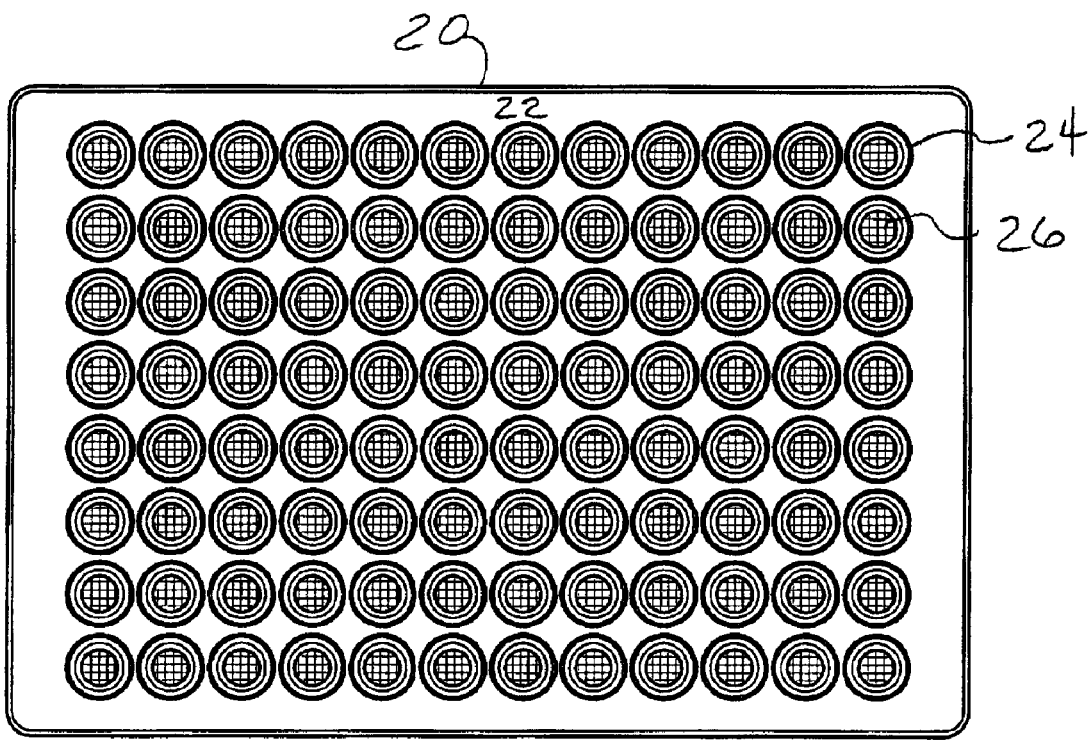
FIG. 3 is a top down view of the separation barrier shown FIG. 2.

In a generally presently preferred embodiment of the invention as shown in FIGS. 2 and 3, the separation barrier 20 comprises a barrier plate 22 with one or more wells 24 which have at least a portion of each well consisting of an open mesh 26. The barrier plate can be a substantially planar structure having therein a plurality of meshed wells to be inserted simultaneously into a plurality of wells of sample to be separated by virtue of the plurality of meshed wells being affixed to or part of the substantially planar structure. The wells are generally vertically disposed with respect to the large plane of the barrier plate. If a single well is to be used, the plate can simply be a ring about the top of a meshed well or a well having a bottom that has an open mesh.

The separation barrier wells with mesh are shaped and sized with sufficient clearance to fit into whatever containers or wells the samples to be separated are in without sticking or causing turbulence in the sample during insertion. Too much clearance allows less access to supernatant and allows the more dense centrifuged materials to "relax" or disburse into supernatant fluid, thereby making a smaller quantity of uncontaminated supernatant available.

The size and shape of the barrier plate and position of the wells (if a plurality of wells is used) will therefore depend upon the size and shape of the container or array of wells holding the samples to be separated. Although the wells are typically cylindrical having either a flat, V-shaped, rounded or conical bottom, other shapes can be used in the practice of the invention. In one particularly useful application of the invention, the separation barrier 20 which is shown in FIG. 2, the barrier plate 22 has wells 24 which correspond to the wells 28 in a microtiter plate 30 which is manufactured for holding samples to be centrifuged. Commonly used microtiter plates include those commercially available such as those with 96 wells, each with a total well volume of about 300 $\mu L$, arranged in rows and columns in each rectangular plate. Other commonly used microtiter plates have 96 wells, each with a total well volume of about 190 $\mu L$, arranged in rows and columns in each rectangular plate.

Barrier plates with wells of varying shapes, depths or diameters could be used by aligning and conforming the wells of the barrier plate to the wells in an array of sample-holding wells. Microtiter plates with raised wells can also be used if desired by conforming the depth of the barrier plate wells to the increased depth of the microtiter plate wells.

The mesh size selected for practice of the invention will vary according to the sizes of the biological materials to be separated; the particular biological materials to be separated will depend upon the specific application for which the invention is employed. Generally, considering any of a great variety of purposes and materials to be separated, the mesh size of open widths can range from about 0.001 inch to about 0.5 inch. For most applications such as separation of cell components, a mesh size of open widths in the range from about 0.005 inch to about 0.05 inch is generally useful. For isolation and collection of cell components such as DNA, a mesh size in the range from about about 60 squares of 0.0075 gauge wire/$cm^2$ to about 50 squares of 0.009 gauge wire/$cm^2$ is presently preferred.

The invention separation barriers can be made of any of a large variety of materials. Any material of sufficient integrity and stiffness to permit it to be inserted into the sample container or wells and one that will not react with, contaminate or otherwise affect the samples to be separated can be used. Material compatible with the processing conditions the sample is subjected to is needed. E.g., a heat resistant material might be necessary when there is a need to rapidly dry samples after rinsing or if the process requires heat treating of the sample. The mesh portion of the separation barrier can be made of a material different from the material used for the barrier plate so long as it is a material which can be affixed to the plate material or the rest of a well which is solid.

Examples of materials useful for the invention separation barriers include, but are not limited to, stainless steel, ceramics, glass, quartz, and any of a large variety of plastics such as polycarbonate, polypropylene, polystyrene, Plexiglass™, Nalgene™, and Teflon™. Composite materials and layered materials such as metals coated with plastics are also useful. Generally barrier plates made of materials which are not reactive with the sample or any treating fluids are required for maintaining purity of the samples.

After centrifuging of the sample containing the biological material to be separated, the barrier plate with meshed wells or the single meshed well is inserted into the sample container or containers to a depth sufficient to separate the denser materials from the maximum amount of supernatant.

A clean catch of supernatant is withdrawn from the liquid above the barrier well which has been inserted into the container holding the centrifuged sample. This can be done using any suitable means, depending upon the density and particle sizes in the supernatant to be collected. A pipette, needle, syringe or suitable suction or transfer device can be used. Presently preferred for withdrawing supernatant containing DNA is a graduate syringe with a needle coated with non-reactive material, or, if a microtiter plate with a plurality of wells is used, a sample transfer robot with an array of a plurality of syringes with needles arranged to have each collection syringe contact the fluid in each well of the microtiter plate. One such transfer robot is that commercially available from Robbins Scientific of Sunnyvale, Calif., as the Hydra™ 96 Microdispenser. The Hydra™ 96 is specifically designed for use with the 96-well microtiter plates also commercially available from Robbins Scientific.

The withdrawn sample then can be transported to subsequent experimental or storage steps.

A significant advantage of the invention apparatus is that the separation barrier can be reused. After the desired amount of supernatant is withdrawn with the barrier mesh in place in the sample container, the separation barrier can be lifted from the sample container, rinsed or washed, dried and sterilized as needed.

The invention apparatus can be used to carry out the invention process in a controlled atmosphere when needed for isolation of bioactive samples.

The process of removing a container holding a centrifuged sample from a centrifuge, positioning it so that the separation barrier can be submerged into the supernatant, withdrawing a portion of the supernatant, and removing the separation barrier from the centrifuged sample container can be reliably automated using computerized equipment known in the art.

When using the invention apparatus and method in applications such as separation of supernatant from denser cell materials, shorter centrifuging times are generally necessary to obtain equally pure samples uncontaminated with denser cell materials.

It has also been found that needles, syringes, or small diameter tubes or pipettes used for withdrawing samples of supernatant remain free from denser biological materials such as cell debris and therefore require fewer washing steps between uses. The reduction in the centrifuging times and the reuse of needles, syringes, tubes or pipettes with fewer washes results in significant improvement in efficiency when preparing large quantities of samples.

EXAMPLE

In an example which demonstrates operability of the invention apparatus and method, the invention was employed in the retrieval of supernatant samples during a cell-lysate-based separation procedure. Plasmid DNA was retreived from host cell cultures for DNA template preparation in the following manner.

In accordance with the solid-phase reversible immobilization method of Hawkins et al., for DNA purification: (a) a culture containing plasmid DNA was grown; (b) the cells from the culture were lysed; (c) the lysate containing the cells was centrifuged; (d) supernatant was recovered from the centrifuged lysate; (e) plasmid DNA from the supernatant was bound to carboxyl coated magnetic particles, washed and subsequently separated from the supernatant solution; (f) a gel of the plasmid DNA is deposited on a 1% agarose gel plate and buffered to provide negatively charged ions; (g) the buffered samples were electrophoretically treated to cause DNA and size markers, if used, to migrate into gel; (h) the gel was stained for viewing on an agarose gel plate under UV light; in accordance with the following procedures.

In one set of 96 samples, the invention method and apparatus was used to maintain the unstable separation of denser cell materials from the supernatant during the period of time between completion of step (c) and completion of step (d).

The lysate containing the cells was centrifuged at 2,800×g for 60 minutes at 4° C. on a Jouan™ GS-4 centrifuge in a microtiter plate 30 similar to the one illustrated in FIG. 2.

The microtiter plate 30 was a Greiner™ U-bottom well microtiter plate (commercially available from Intermountain Scientific) with an array of 96 wells 28, each with a total volume of 200 µL and a working volume of 185 µL in which the centrifuged lysate was contained.

After centrifuging, lysate in each of the wells in the microtiter plate was layered such that a layer of denser cell materials such as broken cell walls, cell membranes, mitochondria, and ribosomes was in the bottom of each well 28 and above the layer of denser cell materials was a layer of supernatant containing less dense cell materials and the target plasmid DNA material.

A separation barrier 20 with a barrier plate 22 with an array of 96 barrier meshes 26 having a mesh size of 50 squares of 0.009 gauge wire/cm$^2$ had been custom designed in accordance with the invention to have dimensions to conform to those of the microtiter plate 30. With the centrifuged lysate still in the wells of the microtiter plate 30, the separation barrier 20 was positioned with respect to the microtiter plate 30 so that the array of projecting meshes 26 of the barrier plate 20 were inserted into the wells 28 of the microtiter plate 30 to a depth above the layer of denser cell materials at the bottoms of the wells 28 of the microtiter plate 30. The separation barrier was held in place by gravity.

The position of the separation barrier 20 with the array of barrier meshes 26 maintained a physical barrier between the sedimented cell debris of the first layer and the supernatant layer, allowing for a clean and easy retrieval of the supernatant without contamination with cell debris or clogging of the Hydra™ 96 transfer robot needles (commercially available from Robbins Scientific) used to withdraw the supernatant.

A 100 µL aliquot of the withdrawn supernatant was transferred to each of the 96 wells of a clean microtiter dish. 15 µL of a 1:10 dilution of concentrated carboxyl-coated magnetic beads, commercially available as Seradyn™, was added to each of the 96 wells containing supernatant sample. Then 125 µL of a 2.5 molar solution of sodium chloride in 20% polyethylene glycol was added to each of the 96 wells of the microtiter dish containing the supernatant. Mixing was accomplished by gently shaking the microtiter dish for about 3 minutes. The mixtures then were allowed to sit for 10 minutes to permit binding of the plasmid DNA to the carboxyl-coated magnetic particles.

An array of 96 magnets arranged so that one magnet was associated with each well of the microtiter plate was placed in contact with the bottoms of the wells of the microtiter plate for a period of 10 minutes. The lysate supernatant cleared as the magnets attracted the carboxyl-coated magnetic particles with the associated plasmid DNA.

A Hydra™ 96 transfer robot was used to remove the fluid from the microtiter plate, leaving the plasmid bound to the carboxyl-coated magnetic particles in the bottom of the wells of the microtiter plate. Three 70% ethanol washes were used to remove any residual supernatant from the carboxyl-coated magnetic particles with the associated plasmid DNA. After the third wash, the carboxyl-coated magnetic particles with the associated plasmid DNA was allowed to air dry at ambient temperature and pressure for 5 minutes. 50 µL of distilled water was added to each well of the microtiter plate containing the samples. The array of magnets was removed from the bottom of the microtiter plate. A foil cover was placed so as to seal the tops of the open wells from the atmosphere and the samples were mixed by shaking for 10 minutes, the held at 93° C. for 35 minutes to dissociate the plasmid DNA from the carboxyl-coated magnetic particles.

After heating, the microtiter plate of samples was cooled to room temperature, then centrifuged for 1 or 2 minutes to remove condensate from the foil cover.

The array of 96 magnets was once again placed into contact with the bottoms of the wells of the microtiter plate to aggregate the carboxyl-coated magnetic particles at the bottoms of the wells. An aliquot of 2 µL of sample from each microtiter plate well was combined with 98 µL of Bromophenol Blue™ tracking dye (glycerol solution) to form a solution of the DNA. 5 µL of the DNA from each well of the microtiter plate was transferred into the wells of a 1% agarose gel and buffered with 500 ml tris-borateEDTA.

The buffered samples were electrophoretically treated in an electrophoresis unit by contacting the samples on the agarose gel with 125 volts at 4 ° C. for a period of 2 hours. After electrophoresis, the gel was stained by mixing with a solution of 5 μg of ethidium bromide in 1 L distilled water for 1 hour.

The stained gel was viewed by placing the agarose gel plate under UV light to enable visualization by fluoresence of the plasmid DNA fragments. A gel photograph for more permanent viewing was taken of the fluoresced DNA product obtained using this procedure. The brightness of fluoresced ethidiun bromide stained DNA samples is directly proportional to the yield or concentration of the DNA samples in the gel.

A second set of 96 control samples was made in accordance with the solid-phase reversible immobilization method of Hawkins et al., for DNA purification in the same manner described above in this example, except that the invention step of inserting the separation barrier into the microtiter plate was omitted.

The stained DNA product obtained using the control procedure was visually inspected and a gel photograph was made of the product made using the control procedure. In a comparison of the plasmid DNA obtained using the invention device and method with the plasmid DNA obtained from the control runs, it can be seen that the amount of plasmid DNA samples that were lost or partically lost due to plugging of needles or due to contaminants interfering with the binding of the plasmid DNA to the carboxyl-coated magnetic particles is significantly fewer when the invention separation barrier is used.

While the apparatuses and methods of this invention have been described in detail for the purpose of illustration, the inventive apparatuses and methods are not to be construed as limited thereby. The claims of this patent are intended to cover all changes and modifications within the spirit and scope thereof.

INDUSTRIAL APPLICABILITY

The separation barriers and methods of this invention can be used any time there is a need to separate centrifugable biological materials or sedimentation based methods are used when there is an unstable sediment involved. The invention is particularly useful for separating plasmid DNA from the rest of cells.

What is claimed is:

1. A method for separating different sized biological materials to increase throughput of sampling, comprising the following steps in the order named:
   a. centrifuging said biological materials in a container;
   b. inserting a separation barrier into said container to separate biological materials with a size small enough to pass through said separation barrier from biological materials with a size too large to pass through said separation barrier;
   c. withdrawing a portion of said biological materials from only one side of said separation barrier.

2. The method of claim 1 wherein said separation barrier is inserted into said container and into a supernatant to a level above aggregated biological materials that will prevent movement of said aggregate biological materials through said separation barrier when a sample of said supernatant is withdraw from the side of said separation barrier opposite from said aggregate biological materials.

3. The method of claim 1 wherein said container is a microtiter plate have one or more sample wells and said separation barrier is a plate having one or more depending sleeves that conform to the inside of said sample wells.

4. The method of claim 2 wherein said supernatant includes plasmid DNA therein.

5. The method of claim 1 further comprising:
   d. withdrawing said separation barrier from said container;
   e. washing said separation barrier; and
   f. re-using said separation barrier.

* * * * *